United States Patent [19]

Jarreau et al.

[11] 4,410,525
[45] Oct. 18, 1983

[54] ALKOXY PYRAZOLE DERIVATIVES AND COMPOSITIONS

[75] Inventors: François X. Jarreau, Versailles; Jean-Jacques Koenig, Vernou La Celle sur Seine, both of France

[73] Assignee: Establissements Nativelle S.A., Paris, France

[21] Appl. No.: 427,344

[22] Filed: Sep. 29, 1982

[30] Foreign Application Priority Data

Oct. 2, 1981 [FR] France .................... 81 18596

[51] Int. Cl.³ ............. A61K 31/535; A61K 31/415; C07D 413/12; C07D 231/20
[52] U.S. Cl. ................. 424/248.57; 424/248.58; 424/250; 424/267; 424/272; 424/273 P; 544/140; 544/371; 546/211; 548/215; 548/240; 548/336; 548/374; 548/377; 260/245.6
[58] Field of Search ............. 544/140, 371; 546/211; 548/215, 240, 336, 374, 377; 260/245.6; 424/248.57, 248.58, 250, 267, 273 P, 272

[56] References Cited

U.S. PATENT DOCUMENTS 4,330,544  5/1982  Jarreau et al. ............. 424/248.56

Primary Examiner—Robert W. Ramsuer
Attorney, Agent, or Firm—Sughrue, Mion, Zinn, Macpeak and Seas

[57] ABSTRACT

The invention relates to 3-aryl-5-alkoxy-pyrazoles, represented by general formula (I):

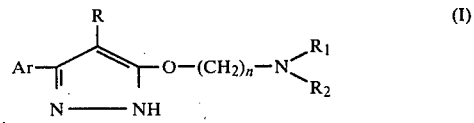

wherein Ar represents an aryl group which may be substituted; R represents a hydrogen atom or an alkyl, phenyl or benzyl group; $R_1$ and $R_2$ which may be the same or different, each represent a hydrogen atom or an alkyl group, or together form a 5 or 7 membered heterocyclic ring with the nitrogen atom to which they are attached; and n is an integer of from 1 to 4; and the pharmaceutically acceptable acid salts thereof, useful in particular, in the treatment of cardiac arrhythmias.

7 Claims, No Drawings

ALKOXY PYRAZOLE DERIVATIVES AND COMPOSITIONS

FIELD OF THE INVENTION

The present invention relates to new pyrazole derivatives, a process for their preparation, as well as their medicinal use.

BACKGROUND OF THE INVENTION

The pyrazole derivatives of the present invention are 3-aryl-5-alkoxy-pyrazoles represented by general formula (I):

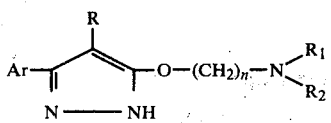
(I)

wherein Ar represents an aryl group, substituted as necessary; R represents a hydrogen atom or an alkyl, phenyl or benzyl group; $R_1$ and $R_2$, which may be the same or different, each represent a hydrogen atom or an alkyl group, or together form a 5 to 7 membered heterocyclic ring with the nitrogen atom to which they are attached; and n is an integer of from 1 to 4; and the pharmaceutically acceptable salts.

The invention also provides a process enabling the preparation of the derivatives of general formula (I) from easily accessible, known starting materials, providing a good yield.

The invention even further provides the use of the pyrazole derivatives of general formula (I) and their pharmaceutically acceptable salts, in human or veterinarian medicine, in particular for the treatment of cardiac arrhythmias.

The aryl group represented by Ar in general formula (I) can be, in particular, a phenyl group which may be substituted by one or more halogen atoms or alkyl, alkoxy, cyano, nitro or hydroxy groups. R can represent a hydrogen atom or a linear or branched alkyl group, such as methyl, ethyl, isopropyl, n-butyl, t-butyl, isoamyl, etc., or a phenyl or benzyl group.

When $R_1$ and $R_2$ form a heterocyclic ring with the nitrogen atom to which they are attached, this heterocyclic ring can be a group completed by carbon atoms, for example a pyrrolyl, pyrrolidinyl, piperidyl, azepinyl group, etc. This heterocyclic ring can also contain one or more other heteroatoms such as nitrogen and oxygen, and for example oxazolidinyl, pyrazolyl, piperazinyl, imidazolyl, morpholinyl, pyrazolinyl groups, etc., are representative.

In general formula (I) above, Ar preferably represents a phenyl group, or a phenyl group substituted with one or more halogen atoms such as chlorine, bromine or fluorine, and, for example, a p-chlorophenyl group or a 3,4-dichlorophenyl group. R preferably represents a hydrogen atom, a lower alkyl group with 1 to 4 carbon atoms, such as a methyl, ethyl or propyl group, or a benzyl group. $R_1$ and $R_2$ preferably represent a lower alkyl group with 1 to 4 atoms, such as a methyl or isopropyl group, $R_1$ being a hydrogen atom whereas $R_2$ is an alkyl group, or the contrary, or together form a heterocyclic group as described above and, more particularly, a pyrrolidinyl, piperidyl, oxazolidinyl, piperazinyl or morpholinyl group. n preferably is 2 or 3.

The 3-aryl-5-alkoxy-pyrazoles of the present invention exist in several forms represented by formula (I) above and formulae (IA) and (IB) below:

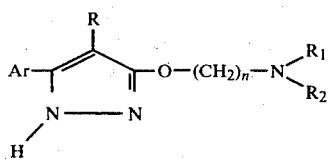
(IA)

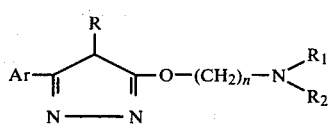
(IB)

The (I) and (IA) forms are predominant, but external factors may shift the equilibrium towards the (IB) form. The invention, of course, relates to the 3-aryl-5-alkoxy-pyrazoles in all the forms (I), (IA) and (IB) shown above.

The invention also provides salts of the pyrazole derivatives represented by general formula (I) above, and in particular, the pharmaceutically acceptable salts obtained by reacting a conventional mineral or organic acid, such as hydrochloric, sulfuric, lactic, oxalic, citric, phosphoric, stearic, maleic or tartaric acid, etc., with the derivative. The reaction can be carried out using conventional techniques, the acid and the derivative generally reacting in substantially stoichiometric proportions.

The pyrazole derivatives in accordance with the invention, shown by general formula (I), can be prepared from pyrazolones of formula (II):

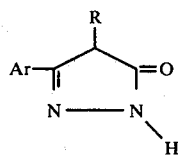
(II)

wherein Ar and R have the same meaning as in formula (I), by alkylation in a basic medium with a haloalkylamine of general formula (III):

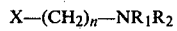

$$X-(CH_2)_n-NR_1R_2 \qquad (III)$$

wherein X represents a halogen atom such as chlorine or bromine, and n, $R_1$ and $R_2$ have the definitions indicated in general formula (I).

The 3-aryl pyrazolones of formula (II) used as starting materials are known compounds which can be prepared in accordance with conventional techniques, such as are described for example in *The Chemistry of Heterocyclic Compounds*, Weissberger, Ed., Intersciences Publ., (1964).

The alkylation reaction of the 3-aryl pyrazolones of formula (II) with the haloalkylamines of formula (III) can be carried out in a basic medium in the presence of a base such as a hydride, an amide, a carbonate or an alkaline metal alkoxide or an amine, in an appropriate organic solvent.

The reaction can, for example, be carried out in the presence of sodium hydride, sodium amide, potassium hydride, sodium ethylate, potassium carbonate, sodium carbonate, diethylamine, triethylamine, etc., in a solvent selected from among dimethylformamide, dimethylsulfoxide, dioxane, tetrahydrofuran, an alcohol such as methanol or ethanol, and acetone. When the solvent is an alcohol, it may be preferable to use a corresponding alkoxide as a base, for example, sodium ethoxide in ethanol. In accordance with the invention, sodium hydride in dimethylformamide, potassium carbonate in dioxane or sodium ethoxide in ethanol are preferably used.

The reaction can take place at ambient temperature, but it may be preferable to heat the reaction mixture to a temperature of between 30° and 100° C., and preferably between 40° and 70° C., in order to accelerate the reaction.

In accordance with a preferred method for the process of the invention, the pyrazolone of formula (II) is dissolved in an organic solvent in a nitrogen atmosphere, a base such as sodium hydride, potassium carbonate or sodium amide is added, the mixture is then heated slightly and the haloalkylamine of formula (II) is added progressively. The solvent is removed by evaporation under reduced pressure and the product obtained is purified using conventional acido-basic or chromatographic extraction techniques.

The haloalkylamines of fomrula (III), which are used to carry out the alkylation of the pyrazolones of formula (II) in accordance with the process of the invention, are generally commercially available in their hydrochloride forms. At the time of use, it may be preferable to transform these hydrochlorides into corresponding bases, by dissolving them in a solution saturated with potassium carbonate and carrying out an extraction, in accordance with the technique described in Fieser and Fieser, *Reagents for Organic Synthesis*, No. IV, John Wiley & Sons (1974).

N-(2-chloroethyl)-dimethylamine, N-(3-chloropropyl)-dimethylamine or N-(2-chloroethyl)-diisopropylamine, or even heterocyclic haloalkylamines such as N-(2-chloroethyl)-pyrrolidine, N-(2-chloroethyl)-piperidine, N-(3-chloro-propyl)-morpholine, N-(3-chloropropyl)-piperidine, etc., may in particular be cited as examples of useful haloalkylamines which can be used in accordance with the invention.

In accordance with one embodiment of the present invention, the pyrazole derivatives of general formula (I) can be prepared from an ethyl aroylacetate of general formula (IV):

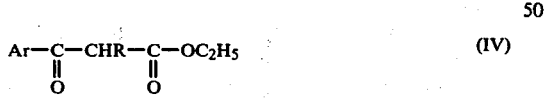

wherein Ar and R have the same meaning as in formula (I), which is transformed by transesterification using an aminoalcohol of formula (V):

wherein n, $R_1$ and $R_2$ have the same meaning as in formula (I), in order to obtain a compound of formula (VI):

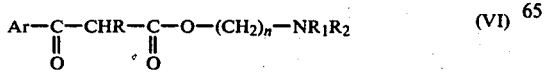

on which cyclization is carried out using hydrazine in an acid medium, yielding the derivative of general formula (I).

The transesterification enabling the transformation of the ethyl aroylacetate of formula (IV) into the ketonic ester of formula (VI) is preferably carried out by heating in a solvent enabling azeotropic distillation. Moreover, it is preferable to conduct the reaction in the presence of an acid catalyst. The solvent can, for example, be a hydrocarbon such as toluene or xylene.

The cyclization reaction using hydrazine in an acid medium, for example, in concentrated hydrochloric acid or a sulfuric acid medium, can be carried out in accordance with a technique analogous to that of H. J. Backer and W. Meier, *Rec. Trav. Chim. P. B.* 45, 428 (1926).

The following examples illustrate the invention without limiting the scope thereof.

EXAMPLE 1

3-p-Chlorophenyl-5-dimethylaminopropoxy-pyrazole 9.5 g of 3-p-chlorophenyl-pyrazolone in 70 ml of dioxane were placed in a 500 ml flask fitted with an agitator, a thermometer, a condenser, a flow tube and a nitrogen inlet. Under a nitrogen atmosphere, it was brought to reflux and 4 g of potassium carbonate was added. After 1 hour of heating under reflux, 7.2 g of 1-dimethylamino-3-chloropropane was added while maintaining the reaction medium under reflux. The addition was carried out progressively for 45 min. The mixture was maintained at reflux for approximately 4 hours, then acido-basic extractions were carried out using conventional techniques after removal of the solvent by vacuum evaporation.

After recrystallization in hexane, then in isopropyl ether, 6.6 g of 3-p-chlorophenyl-5-dimethylamino-propoxypyrazole was obtained (yield 47%).

Melting Point: 114° C. (isopropyl ether)

IR Spectrum (Nujol) $\nu = 3130$, 3100, 1510, 1490 $cm^{-1}$

NMR Spectrum (CDCl$_3$) $\delta = 1.7$–2.7 (4H), 2.2 (s, 6H), 4.0 (t, 2H), 5.8 (s, 1H), 7.3 (q, 4H), 11.2 (s, 1H) ppm The maleate of the above compound was prepared by the action of maleic acid in ethanol, in accordance with conventional techniques.

Melting Point: 155° C.

EXAMPLE 2

3-Phenyl-4-methyl-5-pyrrolidinoethoxy-pyrazole

As in Example 1, 8 g of 3-phenyl-5-pyrazolone was placed in 60 ml of dioxane and heated at reflux under a nitrogen atmosphere, then 3.9 g of potassium carbonate was added. The reaction mixture was maintained at reflux for approximately 1 hour, and 13 g of N-(2-chloroethyl)pyrrolidine was added progressively.

After 4 hours of reaction while maintaining the mixture at reflux, the solvent was removed by vacuum evaporation, and extraction was carried out.

After recrystallization in cyclohexane, 3.5 g of 3-phenyl-4-methyl-5-pyrrolidinomethoxy-pyrazole was obtained (yield 26%).

Melting Point: 88° C. (cyclohexane)

Thin Layer Chromatography (TLC):

Rf=0.4 (ethyl acetate+10% diethylamine).

The corresponding maleate, obtained by conventional techniques, had a melting point of 158°–159° C. (ethanol).

EXAMPLE 3

3-p-Chlorphenyl-5-piperidinopropoxy-pyrazole 19.4 g of 3-p-chlorophenyl-pyrazolone was placed in 60 ml of anhydrous dimethylformamide in a 500 ml flask fitted with a condenser with a calcium chloride tube, a flow tube, a thermometer and a nitrogen input. Then the solution was degasified by bubbling nitrogen therethrough. The mixture was cooled to approximately 5° C. and 2.8 g. of sodium hydride was added. The temperature of the mixture was allowed to return to ambient temperature, then was heated progressively to 40° C. 17.4 g of 3-chloropropyl-piperidine was added dropwise and allowed to react for approximately 10 hours.

After vacuum evaporation of the solvent, acido-basic extraction, and recrystallization in isopropanol, 10.7 g of 3-p-chlorophenyl-5-piperidinopropoxy-pyrazole was obtained (yield 30%). In addition, during the purification, approximately 25% of the starting 3-p-chlorophenyl-5-pyrazolone was recovered as well as approximately 3 g of 3-p-chlorophenyl-2-piperidinopropyl-pyrazolone as a secondary product.

Melting Point: 140° C. (isopropanol)
IR Spectrum (Nujol): $v = 3250, 1510$ cm$^{-1}$
NMR Spectrum (CDCl$_3$): $\delta = 1.6$ (6H), 2.1 (2H), 2.6 (6H), 4.3 (t, 2H), 6.2 (s, 1H), 7.8 (g, 4H) ppm.

EXAMPLE 4

3-Phenyl-4-methyl-5-morpholinoethoxy-pyrazole

Using the process of Example 1, 8 g of 3-phenyl-5-pyrazolone was placed in 60 ml of dioxane. This was heated at reflux and 4.1 g of potassium carbonate was added, then, progressively, 7.8 g of N-(2-chloroethyl)-morpholine was added.

When the reaction was completed, after extraction and recrystallization in isopropanol, 5.1 g of 3-phenyl-4-methyl-5-morpholinoethoxy pyrazole was obtained (yield 36%).

Melting Point: 100° C. (isopropanol)
TLC: Rf = 0.60 (ethyl acetate + 10% diethylamine)

The corresponding maleate, prepared by conventional techniques, by action of maleic acid in ethanol, had a melting point of 156° C.

EXAMPLE 5

3-Phenyl-5-morpholinoethoxy-pyrazole

In a 250 ml flask fitted with an azeotropic distillation apparatus and a flow tube, 9.6 g of ethyl benzoylacetate and 19.7 g of N-(2-hydroxyethyl)morpholine were dissolved in 100 ml of toluene.

This was brought to the boiling point, the toluene-ethanol azeotrope was distilled and at the same time pure toluene was added. The reaction was practically totally complete after approximately 4 hours. The toluene was washed with distilled water, then with water saturated with calcium chloride, and was dried over sodium sulfate and evaporated until dry. In this manner 12.4 g of morpholinoethyl benzoylacetate was obtained in the form of a yellow oil (yield 90%).

0.3 g of hydrated hydrazine, 15 ml of absolute ethanol and 1.6 ml of concentrated hydrochloric acid were placed in a 100 ml flask. This was heated to reflux and 1.4 g of morpholinoethyl benzoylacetate obtained as described above was added. The mixture was maintained at reflux for approximately 2 hours, and the reaction was then practically totally complete. The ethanol was vacuum evaporated, then the reaction product was flooded with water and extracted with chloroform in order to isolate approximately 0.1 g of 5-ethoxy-3-phenyl-pyrazole. The aqueous phase was rendered alkaline and then extracted with chloroform to yield 0.5 g of 3-phenyl-5-morpholinoethoxy-pyrazole (yield 36%).

Melting Point: 100° C. (isopropanol)
IR Spectrum (Nujol) $v = 3260, 1595, 1510$ cm$^{-1}$

EXAMPLES 6 to 23

Using the process of Example 1, but appropriately modifying the starting pyrazolone and haloalkylamine, the products indicated in the following table, as well as their salts, whose characteristics (melting point, recrystallization solvent and thin layer chromatography with an eluent composed of ethyl acetate to which 10% diethylamine was added) are also set forth in same table.

EXAMPLES 6 to 23

| Ex. | Ar | R | NR$_1$R$_2$ | n | MP (°C.) | Rf* | Salt | MP (°C.) |
|---|---|---|---|---|---|---|---|---|
| 6 | -C$_6$H$_4$-Cl | H | -N(piperidine) | 2 | 117 | 0.65 | Tartrate | 212 |
| 7 | -C$_6$H$_4$-Cl | H | -N(pyrrolidine) | 2 | 128 | 0.60 | Maleate | 190 |
| 8 | -C$_6$H$_5$ | H | -N(CH$_3$)$_2$ | 3 | (oil) | 0.45 | Maleate | 115 |
| 9 | -C$_6$H$_5$ | H | -N(piperidine) | 2 | 70–72 | 0.55 | Maleate | 139 |

-continued

EXAMPLES 6 to 23

| Ex. | Ar | R | NR₁R₂ | n | MP (°C.) | Rf* | Salt | MP (°C.) |
|---|---|---|---|---|---|---|---|---|
| 10 | 4-Cl-C₆H₄- | H | -N(morpholine) | 2 | 120 | 0.60 | Maleate | 170 |
| 11 | C₆H₅- | CH₃ | -N(piperidine) | 2 | 80 | 0.3 | Maleate | 143 |
| 12 | C₆H₅- | H | -N(pyrrolidine) | 2 | (oil) | 0.35 | Maleate | 131 |
| 13 | C₆H₅- | H | -N(piperidine) | 3 | (oil) | 0.55 | Oxalate | 137 |
| 14 | C₆H₅- | CH₃ | -N(piperidine) | 3 | (oil) | 0.5 | Maleate | 116–117 |
| 15 | C₆H₅- | CH₃ | -N(CH₃)₂ | 3 | (oil) | 0.3 | Maleate | 155–158 |
| 16 | 4-Cl-C₆H₄- | CH₃ | -N(morpholine) | 2 | 112 | 0.5 | Hydrochloride | 210 |
| 17 | 4-Cl-C₆H₄- | CH₃ | -N(CH₃)₂ | 3 | 98 | 0.45 | Tartrate | 71 |
| 18 | 4-Cl-C₆H₄- | CH₃ | -N(pyrrolidine) | 2 | 108 | 0.70 | Maleate | 165 |
| 19 | 4-Cl-C₆H₄- | CH₃ | -N(piperidine) | 3 | 89 | 0.6 | Tartrate | 102–118 |
| 20 | 3,4-Cl₂-C₆H₃- | H | -N(pyrrolidine) | 2 | 128 | 0.50 | Maleate | 176 |
| 21 | 4-Cl-C₆H₄- | CH₃ | -N(piperidine) | 2 | 113 | 0.55 | Tartrate | 186 |

| | | | -continued | | | | | |
|---|---|---|---|---|---|---|---|---|
| | | | EXAMPLES 6 to 23 | | | | | |
| Ex. | Ar | R | NR₁R₂ | n | MP (°C.) | Rf* | Salt | MP (°C.) |
| 22 | —C₆H₅ | —CH₂—C₆H₅ | —N⟨morpholino⟩ | 2 | (oil) | 0.45 | Tartrate | 152–153 |
| 23 | 2,3-dichlorophenyl | H | —N⟨piperidino⟩ | 3 | 96 | 0.44 | Maleate | 140 |

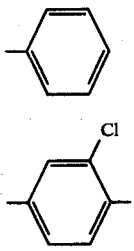

*T.L.C.: Ethyl acetate + 10% diethylamine

Evaluations carried out on the 3-aryl-5-alkoxy-pyrazoles of the invention have revealed interesting pharmacological and toxicological properties rendering them useful in veterinary and human medicine.

TOXICOLOGICAL PROPERTIES

The acute toxicity of the deriatives of the invention were studied by oral administration (P.O) to the mouse (10 animals, 5 males and 5 females per dose) and calculation of the lethal dose 50 (LD 50) in accordance with the method of Litchfield and Wilcoxon (*J. Pharmacol.*, 96, 99–113 (1949)). Table 1 gives the LD 50 values of the derivatives of the invention.

In certain cases, the LD 50 was also studied after intraperitoneal injection (I.P.) of the derivatives.

The results obtained are shown below

TABLE 1

| EXAMPLE No. | LD 50 P.O. (mg/kg) | LD 50 I.P. (mg/kg) |
|---|---|---|
| 1 | 1,000 | 250 to 500 |
| 2 | 500 | — |
| 3 | 700 | — |
| 4 | 750 | — |
| 5 | 1,000 | — |
| 6 | 500 | — |
| 7 | 1,000 | 280 |
| 8 | 1,000 | — |
| 9 | 400 to 800 | — |
| 10 | 1,000 | — |
| 11 | 250 to 500 | 184 |
| 12 | 500 to 1,000 | — |
| 13 | 125 to 250 | — |
| 14 | 250 | — |
| 15 | 500 to 1,000 | — |
| 16 | 500 to 1,000 | 125 to 250 |
| 17 | 500 to 1,000 | 250 to 500 |
| 18 | 750 | — |
| 19 | 250 | 62 to 125 |

PHARMACOLOGICAL PROPERTIES

1. Cardiovascular Tolerance

Cardiovascular tolerance was studied on the isolated guinea pig auricle, on the anesthetized rat and on the anesthetized dog.

On the isolated guinea pig auricle, the preparation enabled the measurement of the contractile force of the auricular myocardium of the guinear pig and the frequency of auricular contractions. At the concentration of 10 μg/ml of bath solution, the derivatives tested caused a decrease in the frequency of the contractions of from 15 to 75% (average: −43.25%) in relation to the pre-treatment control period. At the same concentration, the contraction force varied from 0 to −80% in relation to the control period (average variation −37.5%).

On the anesthetized rat, the derivatives of the invention, administered at doses of 6 to 25 mg/kg, caused a decrease in cardiac frequency (5 to 40%), of the aortic flow, and of the systolic arterial pressure (4 to 60%).

On the anesthetized dog, the results obtained with respect to hemodynamic tolerance are summarized in Table 2 below which indicates the percentages of variation of the hemodynamic parameters in relation to the pre-treatment control period for the derivatives of Examples 2 and 4.

The parameters were recorded by means of:

Catheters connected to pressure sensors (arterial pressure, left ventricular pressure and its first derivative dp/dt);

Electromagnetic flowmeter on the aorta (aortic flow);

Electrocardiograph;

Strain gauge placed on the left ventricular myocardium (force of myocardiac contraction).

The derivatives were injected intraveneously, one dose approximately every 30 minutes and their effects were measured 20 minutes after the completion of the injection (length of the injection 2 minutes).

TABLE 2

| Hemodynamic Effects on the Anesthetized Dog | | | | | |
|---|---|---|---|---|---|
| | DOSES (mg/kg) | | | | |
| EXAMPLE 4 Derivative | 1 | +3 | +10 | +20 | +40 |
| Systolic arterial pressure | 0 | 0 | 0 | 0 | 0 |
| Cardiac frequency | 0 | 0 | 0 | 0 | −18 |
| Cardiac flow | 0 | 0 | −23 | −34 | −11 |
| Systolic volume | 0 | 0 | −23 | −34 | −8 |
| Contraction force of the myocardium | +5 | +10 | +26 | +42 | +52 |
| (dp/dt)l/p | +10 | +2 | −10 | −21 | −10 |
| EXAMPLE 2 Derivative | 0.5 | +1 | +3 | +5 | +10 | +10 |
| Systolic arterial pressure | +4 | 0 | 0 | −8 | −12 | −20 |
| Cardiac frequency | 0 | −8 | −8 | −8 | −8 | −8 |
| Cardiac flow | 0 | −5 | −5 | −20 | −37 | −45 |
| Systolic volume | 0 | +3 | +3 | −12 | −31 | −40 |
| Contraction force of the myocardium | 0 | 0 | −20 | −20 | −10 | −20 |
| (dp/dt)l/p | 0 | −7 | −30 | −30 | −38 | −46 |

Note:
The effects are expressed as a percentage of variation in relation to the pre-treatment The results shown in Table 2, as well as the analogous results obtained with the other derivaties of the present invention, show that the derivatives cause the following modifications in the dog:

Systolic arterial pressure does not change (derivatives of Examples 4 and 9), or drops moderately (derivatives of Examples 2, 14 and 19). Also, for derivative of Example No. 2, this decrease only appears after the cumulative dose of 4.5 mg/kg;

Cardiac frequency does not change (derivatives of Examples 4 and 19), or drops moderately (derivatives of Examples 9, 2 and 14);

Cardiac flow is lowered in all cases. However, this modification remains moderate since a drop of 20% is only reached with cumulative doses greater than 4 mg/kg (derivatives of Examples 4, 9 and 19) or even greater than 9 mg/kg (derivative of Example 2);

The force of ventricular myocardiac contractions increases after the injections of derivative of Example No. 4, does not vary significantly with derivatives of Examples Nos. 9 and 14, decreases with derivatives of Examples Nos. 2 and 19. Here again, this decrease, when it exists, remains moderate (maximum of −20% for derivative of Example No. 2 after injection of 4.5 mg/kg to 29 mg/kg).

These results show that cardiovascular tolerance in the dog is satisfactory since the effects are limited to a moderate drop in cardiac flow whereas the force of myocardiac contractions, systolic arterial pressure and cardiac frequency vary diversely.

2. Electrophysiological Tests

The maximum frequency test carried out studied the maximum stimulation frequency which can cause contraction of an isolated guinea pig auricle placed in a solution containing a derivative of the invention. The measurement was carried out before (control period) and then after introduction of the derivative into the solution.

Table 3 shows the percentages of decrease of the maximum frequency followed, for a concentration of 10 mg/l of each of the derivatives according to the invention. The results obtained show that the derivatives according to the invention increase the auricular refractory period from 12 to 56%.

TABLE 3

| Example | Δ% MFS |
|---|---|
| 1 | −30 |
| 2 | −56 |
| 3 | −53 |
| 4 | −27 |
| 5 | −12 |
| 6 | −46 |
| 7 | −45 |
| 8 | — |
| 9 | −48 |
| 10 | −15 |
| 11 | −52 |
| 12 | −35 |
| 13 | −44 |
| 14 | −40 |
| 15 | −40 |
| 16 | −28 |
| 17 | −32 |
| 18 | −45 |
| 19 | −52 |

In addition, an electrophysiological test was carried out on the dog anesthetized with pentobarbital, with a closed thorax, by means of bipolar catheter-electrodes introduced into the cardiac cavities by transcutaneous veinous and arterial means, so as to measure the sinusal automaticity, the intracardiac conduction times and the effective and functional cardiac refractory periods.

During the electrophysiological study, the derivatives were injected intravenously for 2 minutes for each dose and at 30 minute intervals. The measurement of the various parameters was carried out before the injection of the first dose (control period) and from 10 to 28 minutes after the injection of each dose of the substance. It was noted that the sinusal automaticity was not significantly depressed nor was the conduction speed between the auricles and the auriculo-ventricular knot. On the other hand, conduction slowed down in the His-Purkinje system from the time of the dose of 4.5 mg/kg and it is known that this parameter is very characteristic of the effects of antiarrhythmic medications of Vaughan-Williams Group I (quinidine-like). The effective auricular and ventricular refractory periods lengthen proportionally with the dose administered. The auriculo-ventricular nodal functional refractory period only on the other hand increases moderately and the effects rapidly reach a maximum plateau in the range of doses studied.

3. Antiarrhythmic Tests

The derivatives of the invention were used in the test with aconitine on the rat. For this test, the anesthetized rat was intoxicated by an intravenous perfusion of aconitine (solution of aconitine nitrate: 15 mg/l; speed of perfusion: 0.4 ml/min) while its electrocardiogram was recorded permanently. During perfusion at constant speed, the time necessary for the appearance of ventricular arrhythmias, successively ventricular extrasystoles (ESV), ventricular tachycardium (TV) and ventricular fibrillation (FV) was measured.

The animals were divided into a control group (untreated) and treated group (different doses). The results are expressed as a percentage of prolonging the time of the appearance of the arrhythmias in the treated groups in relation to the control group. This prolongation of arrhythmia appearance time therefore corresponds to myocardiac protection against the arrhythmic effects of aconitine.

Table 4 below gives the results obtained with various derivatives of the present invention.

TABLE 4

| | Injected Dose | VENTRICULAR ARRHYTHMIAS (%) | | |
|---|---|---|---|---|
| Example | mg/kg | ESV | TV | FV |
| 2 | 10 | +32 | +30 | +44 |
| 3 | 10 | +6 | +28 | +46 |
| 4 | 10 | +7 | +22 | +18 |
| 6 | 3 | +13 | +21 | +18 |
| 7 | 10 | +11 | +45 | +32 |
| 9 | 10 | 0 | +28 | +38 |
| 11 | 10 | +10 | +11 | +18 |
| 18 | 10 | +2 | +6 | 0 |
| 19 | 10 | +15 | +15 | +35 |

Cardiac antifibrillatory activity of the derivatives of the invention has been verified on the mouse using the Lawson test, in accordance with the method described by J. W. Lawson, J. Pharmacol. Exp. Therp. 160, 22–31 (1968), and C. Narcisse et al., Ann. Pharm. Fr. 37, 325–330 (1979).

The mice (20 per dose) received an intraperitoneal injection of the derivative 10 minutes before being placed in a chloroform saturated atmosphere. As soon as respiratory arrest occurred, the thorax was opened (5 to 10 seconds) and the state of the heart was checked: presence or absence of ventricular fibrillation. The efficacy dose 50 (ED 50) of the derivative being studied is the dose which protects half the mice against anoxic ventricular fibrillation.

The results in Table 5 below show that the derivatives of the invention possess good antifibrillatory activity.

TABLE 5

| Derivative | ED 50 (mg/kg) |
|---|---|
| 3 | 35 |
| 4 | 46 |
| 5 | 79 |
| 7 | 66 |
| 9 | 44 |
| 11 | 42.5 |
| 14 | 62 |
| 19 | 21.5 |

In addition, the Harris test, carried out on the dog in accordance with the technique described in Circulation, 1, 1318 (1950), shows that the derivatives of the invention cause a decrease in ventricular extrasystoles. By way of example, the number of ventricular extrasystoles per minute decreases by approximately 50% during the 2 hours following the injection of the product, in the case of the derivative described in Example 10. Moreover, the antiarrhythmic effect (myocardiac protection) increases with the size of the dose injected.

Finally, it can be noted that the derivatives of the present invention possess a local anesthetic effect verified on the rabbit cornea (local contact anesthesia) after instillation of an eyewash containing the derivative to be tested. For example, the derivatives described in Examples 2, 3, 4, 6, 7 and 9 are local anesthetics (100% anesthesia) in a solution at 0.25% or 1% by weight.

These results show that the derivatives of 3-aryl-5-alkoxy-pyrazole of the present invention possess advantageous antiarrhythmic properties, as well as electrophysiological properties and good hemodynamic tolerance, permitting their use in human and veterinarian medicine, in particular in the treatment of various forms of cardiac arrhythmias.

The derivatives of the invention and their pharmaceutically acceptable salts can be administered in conventional forms, the active constituent being diluted in an appropriately selectedd pharmacetically acceptable carrier, for example, in the form of tablets, capsules, lozenges, suppositories, injectable solutions or syrups.

By way of example, tablets can be prepared by mixing the derivative of the invention or one of its salts, with one or several solid diluents, such as lactose, mannitol, starch, polyvinylpyrrolidone, magnesium stearate, talc, etc. Where necessary, the tablets may comprise several layers superposed around a nucleus, in accordance with conventional techniques, in order to ensure progressive release or a delayed effect of the active ingredient. The coating may, for example, be composed of one or several layers of polyvinyl acetate, carboxymethylcellulose or cellulose acetophthalate.

The derivative of the invention may also be administered in the form of a syrup or drinkable solution obtained by dissolving the derivative, as necessary in the form of a pharmaceutically acceptable salt, in water or glycerol, for example, and, as necessary, adding a conventional additive such as a sweetener and an antioxidant.

Injectable solutions can be prepared using well-known techniques and can be composed, for example, of a solution containing a derivative of the invention or one of its pharmaceutically acceptable salts, dissolved in bidistilled water, a hydroalcoholic solution, propylene glycol, etc., or a mixture of such solvents. Where necessary, an appropriate additive such as a preservative may be added.

Dosage may vary in accordance with the type of condition treated and the subject being treated. Doses administered daily are generally comparable to those of quinidinic treatments, (kg 5 to 30 mg·kg$^{-1}$orally) but can be adjusted by the practitioner depending upon the circumstances.

While the invention has been described in detail and with reference to specific embodiments thereof, it will be apparent to one skilled in the art that various changes and modifications can be made therein without departing from the spirit and scope thereof.

What is claimed is:

1. A 3-aryl-5-alkoxy-pyrazole represented by general formula (I):

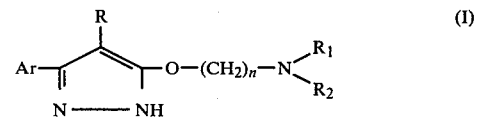

(I)

wherein Ar represents an aryl group which may be substituted; R represents a hydrogen atom or an alkyl, phenyl or benzyl group; $R_1$ and $R_2$, which may be the same or different, each represent a hydrogen atom or an alkyl group, or together form a 5 to 7 membered heterocyclic ring with the nitrogen atom to which they are attached; n is an integer of from 1 to 4; and the pharmaceutically acceptable acid salts thereof.

2. The 3-aryl-5-alkoxy-pyrazole of claim 1, wherein Ar is a phenyl group or a phenyl group substituted with one or more halogen atoms or alkyl, alkoxy, cyano, nitro or hydroxy groups.

3. The 3-aryl-5-alkoxy-pyrazole of claim 2, wherein Ar is a phenyl group, or a phenyl group substituted by one or more chlorine atoms.

4. The 3-aryl-5-alkoxy-pyrazole of claim 1, wherein R is a hydrogen atom, a lower alkyl group with 1 to 4 carbon atoms, or a benzyl group.

5. The 3-aryl-5-alkoxy-pyrazole of claim 1, wherein $R_1$ and $R_2$ each represent a lower alkyl group with 1 to 4 carbon atoms, or together form, with the nitrogen atom to which they are attached, a 5 to 7 membered heterocyclic ring which may contain nitrogen and oxygen atoms as additional heteroatoms.

6. The 3-aryl-5-alkoxy-pyrazole of claim 5, wherein $R_1$ and $R_2$ form, with the nitrogen atom to which they are attached, a pyrrolyl, pyrrolidinyl, piperidyl, azepinyl, oxazolidinyl, pyrazolyl, piperazinyl, imidazolyl, morpholinyl or pyrazolinyl group.

7. A pharmaceutical composition containing a therapeutically effective amount of 3-aryl-5-alkoxy-pyrazole or a pharmaceutically acceptabel salt thereof of claim 1, 2, 3, 4, 5 or 6, and a pharmaceutically acceptable carrier or diluent.

* * * * *

UNITED STATES PATENT AND TRADEMARK OFFICE
CERTIFICATE OF CORRECTION

PATENT NO. : 4,410,525

DATED : October 18, 1983

INVENTOR(S) : Jarreau et al

It is certified that error appears in the above-identified patent and that said Letters Patent is hereby corrected as shown below:

On the title page assignee should read

--(73) Assignee: Etablissements Nativelle S.A., Paris France --.

Signed and Sealed this

Fourth Day of December 1984

[SEAL]

Attest:

GERALD J. MOSSINGHOFF

*Attesting Officer*  *Commissioner of Patents and Trademarks*